United States Patent
Kato et al.

(10) Patent No.: US 8,247,215 B2
(45) Date of Patent: Aug. 21, 2012

(54) APPARATUS FOR INTRODUCING SUBSTANCE INTO CELLS

(75) Inventors: Kouichi Kato, Yokohama (JP); Atsushi Takahashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 249 days.

(21) Appl. No.: 12/522,041

(22) PCT Filed: Jan. 17, 2008

(86) PCT No.: PCT/JP2008/050927
§ 371 (c)(1), (2), (4) Date: Jul. 2, 2009

(87) PCT Pub. No.: WO2008/090937
PCT Pub. Date: Jul. 31, 2008

(65) Prior Publication Data
US 2010/0021986 A1     Jan. 28, 2010

(30) Foreign Application Priority Data
Jan. 26, 2007   (JP) .................................. 2007-016414

(51) Int. Cl.
*C12M 1/00*      (2006.01)
(52) U.S. Cl. ...................................................... 435/283.1
(58) Field of Classification Search .................. None
See application file for complete search history.

(56) References Cited

U.S. PATENT DOCUMENTS

| | | |
|---|---|---|
| 2003/0113833 A1 | 6/2003 | Oka et al. |
| 2005/0112756 A1 | 5/2005 | Nakatani et al. |
| 2005/0221469 A1 | 10/2005 | Nakatani et al. |
| 2007/0059763 A1 | 3/2007 | Okano et al. |
| 2007/0259394 A1 | 11/2007 | Kanome et al. |

FOREIGN PATENT DOCUMENTS

| | | |
|---|---|---|
| JP | 2003-033177 A | 2/2003 |
| JP | 2004-271331 A | 9/2004 |
| JP | 2005-156234 A | 6/2005 |
| JP | 2005-176630 A | 7/2005 |
| JP | 2005-204837 A | 8/2005 |
| JP | 2005-214889 A | 8/2005 |
| JP | 2006-129798 A | 5/2006 |
| WO | 2002/055653 A1 | 7/2002 |

OTHER PUBLICATIONS

Iwan Walev et al., "Delivery of Proteins into Living Cells by Reversible Membrane Permeabilization with Streptolysin-O," Proceedings of the National Academy of Sciences of the United States of America, vol. 98, No. 6, pp. 3185-3190 (Mar. 2001).

*Primary Examiner* — Allison Ford
*Assistant Examiner* — Yvonne Pyla
(74) *Attorney, Agent, or Firm* — Fitzpatrick, Cella, Harper & Scinto

(57) ABSTRACT

Provided is a cell chip for exposing to a portion of each of cells microdroplets dispensed with an inkjet printer or the like in a screening test of the effect of a substance on cells by using an apparatus for introducing the substance into cells including: a cell-immobilizing support including a substrate having through-holes penetrating from one side to the other side of the substrate and including cells immobilized in the through-holes so as to block up the through-holes; a liquid phase region present in contact with one side of the support and including a medium of the cells; and a mechanism present so as to face the other side of the support and imparting a microdroplet to a portion of each of the cells exposed in the openings on the other side.

4 Claims, 4 Drawing Sheets

APPARATUS FOR INTRODUCING SUBSTANCE INTO CELLS

TECHNICAL FIELD

The present invention relates to an apparatus and a method for introducing a substance into cells.

BACKGROUND ART

For the purpose of developing new therapeutic agents and new diagnostic agents, there have been demanded techniques to efficiently evaluate the responses of pharmaceutical candidate substances to cells. In these years, pharmaceutical candidate substances have been frequently synthesized by using combinatorial chemistry techniques, and a large number of types of compounds have been efficiently and systematically prepared. Candidate substances prepared in such ways are frequently small in quantity, accordingly the scale of the cell medium used for evaluation is also made to be of a microscopic size, and when a candidate substance is administered to cells, a microdroplet dispenser such as an inkjet printer is used as the case may be (see Japanese Patent Application Laid-Open No. 2003-033177). In other words, the observation apparatus is made to be of a microscopic size.

For the purpose of injecting medicinal solutions of a drug, a gene or the like into cells, generally adopted in a microinjection method in which a glass pipette with a very thinly tapered tip is pricked into a cell to introduce a medicinal solution like injection. Such a glass pipette is obtained by heating a glass tube with a burner or the like and by pulling the heated glass tube.

Additionally, possible examples of the candidate substances may include various substances such as common chemical substances, peptides, antibody derivatives and nucleic acids. These candidate substances include some substances that display effects only when incorporated into cells. Accordingly, various methods have been reported for the purpose of incorporating candidate substances into cells in medium. Examples of such methods include a method in which a portion of a cell membrane is made to be a semipermeable membrane with streptolysin-O (SLO) to introduce substances into cells (see Japanese Patent Application Laid-Open No. 2006-129798).

DISCLOSURE of THE INVENTION

However, conventional techniques involve the following problems. First, when an inkjet printer is used in a screening test for the purpose of investigating the effects of a candidate substance on cells, a solution of the candidate substance is given to the whole of each cell, and it has been difficult to give only a portion of each cell a dispensing solution. On the other hand, when the microinjection method is used, the insertion of a glass pipette bores a large hole in the cell membrane, and additionally it is difficult to control the insertion depth of the glass pipette. Alternatively, in a case where SLO is given to a cell for the purpose of incorporating a candidate substance into the cell as described in Japanese Patent Application Laid-Open No. 2006-129798, when SLO is made to act on the whole cell, small holes are formed all over the cell membrane, and the intracellular fluid flows outside the cell. Consequently, the nature of the cell is altered so as to disturb the evaluation of the substance.

Accordingly, the present invention takes as its object the provision of an apparatus for introducing a substance into cells by bringing a microscopic amount of a solution into contact with only a portion of each cell and a method for introducing a substance into cells by using the apparatus.

The above-described object can be achieved according to the following:

(i) An apparatus for introducing a substance into a cell including:

a cell-immobilizing support including a substrate having a through-hole penetrating from one side to the other side of the substrate and including a cell immobilized in the through-hole so as to block up the through-hole;

a liquid phase region present in contact with one side of the support and including a medium of the cell; and a mechanism present so as to face the other side of the support and imparting a microdroplet to a portion of the cell exposed in the opening on the other side.

Alternatively, this apparatus may be described as an apparatus for introducing a substance into cells, the apparatus including: a substrate having through-holes capable of being blocked up by immobilized cells; a cell-immobilizing support present in contact with the through-hole openings on one side of the substrate and having a liquid phase region including a medium of the immobilized cells, and an apparatus for administering, from the through-hole openings on the other side of the substrate, a microdroplet to a portion of each of the cells.

(ii) A method for introducing a substance into a cell including the steps of:

immobilizing a cell in the through-hole of a through-hole-including substrate so as to block up the through-hole;

preparing a microdroplet including a substance to be introduced into the cell; and imparting the microdroplet to a portion of the cell exposed in one of the openings of the through-hole.

BEST MODES FOR CARRYING OUT THE INVENTION

Preferred embodiments of the present invention will now be described in detail in accordance with the accompanying drawings. Hereinafter, description is made on the following apparatus and method according to the present invention with reference to specific embodiments: (i) the apparatus for introducing a substance into cells including: a cell-immobilizing support including a substrate having through-holes penetrating from one side to the other side of the substrate and including cells immobilized in the through-holes so as to block up the through-holes; a liquid phase region present in contact with one side of the support and including medium of the cells; and a mechanism present so as to face the other side of the support and imparting a microdroplet to a portion of each of the cells exposed in the openings on the other side; and (ii) the method for introducing a substance into cells including the steps of: immobilizing cells in the through-holes of a through-hole-including substrate so as to block up the through-holes; preparing microdroplets including a substance to be introduced into the cells; and imparting a microdroplet to a portion of each of the cells exposed in one of the openings of each of the through-holes.

Embodiment 1

Structure of a Substrate Having Through-Holes for Immobilizing Cells

Figure 2:
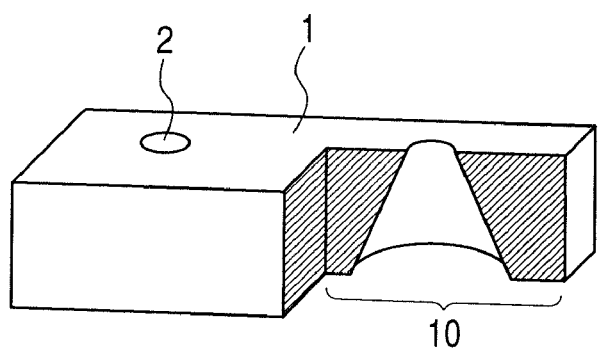
FIG. 2 is a view illustrating a substrate shape example 1 for immobilizing cells.

The structure of the substrate according to the present embodiment is described with reference to FIG. 2.

The substrate 1 immobilizes cells, and the thickness thereof is preferably 5 μm or more and 1 mm or less from the viewpoint that cells can be immobilized and cells can be observed under a microscope with small disturbance. Additionally, from the viewpoint of the convenience in machining for boring of through-holes, the thickness of the substrate is preferably 7.5 μm or more and 100 μm or less. The raw material for the substrate is not limited as long as the substrate can immobilize the cells according to the below described method and does not disturb the intended observation of the cells. Examples of preferable raw materials for the substrate include the thin films of synthetic resins such as polyimide, polyvinylidene chloride, polystyrene, polyethylene and polydimethylsiloxane. Additionally, for the purpose of observing the whole image of each of the cells, the substrate is preferably colorless and transparent, but being transparent is not an indispensable prerequisite.

Figure 3:
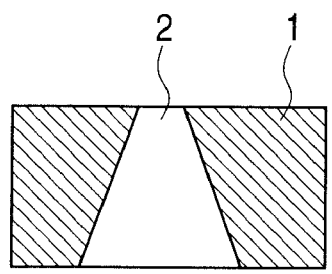
FIG. 3 is a view illustrating the substrate shape example 1 (a plane sectional view of FIG. 2) for immobilizing cells.
Figure 4:
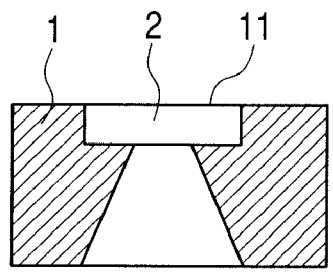
FIG. 4 is a view illustrating a substrate shape example 2 for immobilizing cells.

An opening 2, on the microdroplet addition side, of one of the through-holes bored in the substrate is shown. A three-dimensional section-representing portion 10 of the three-dimensional section of a substrate portion around a through-hole is also shown. FIG. 3 is a lateral view of the three-dimensional section-representing portion 10 of FIG. 2. As shown in the three-dimensional section-representing portion 10 of FIG. 2 and in FIG. 3, the shape of the through-holes (through-holes penetrating from one side to the other side of the substrate) bored in the substrate is preferably a circular truncated cone from the viewpoint of holding the cells in the through-holes. Alternatively, the shape of the through-holes may be a shape other than the circular truncated cone such as a cylinder, a truncated pyramid, a rectangular column or a combination of these shapes. However, the opening (the above-described opening on "the other side") 2 of each of the through-holes is characterized by having a size capable of being blocked up by the cell to be used for observation. For example, when the opening 2 is set to be circular, the diameter thereof is preferably 1 μm or more and 10 μm or less. The size of the opening 2 has only to meet the above-described cell-holding conditions, and may be appropriately regulated according to the target cells. From the viewpoint of the design concept, in consideration of the fact that the diameters of common cells are 10 to 20 μm, the size of the opening 2 is preferably set to be 0.785 μm$^2$ or more and 78.5 μm$^2$ or less. As shown in FIG. 4 illustrating a sectional view of the substrate, a minute recess 11 (in the figure, a cylindrical recess is intended) for holding a microdroplet may be formed directly above the opening 2. When such a recess is formed, "the size of the opening 2" is defined as the size of the opening on the bottom of the recess (the size of the opening as found in the boundary between the cylinder and the circular truncated cone). The fabrication method of the through-holes possessed by the substrate may be appropriately selected from the hitherto reported techniques. For example, a femtosecond pulse laser may be used for boring processing, and a substrate with through-holes bored therein may also be fabricated by using semiconductor fabrication techniques.

Embodiment 2

Cells Immobilized in the Through-Holes in the Substrate

Figure 5:
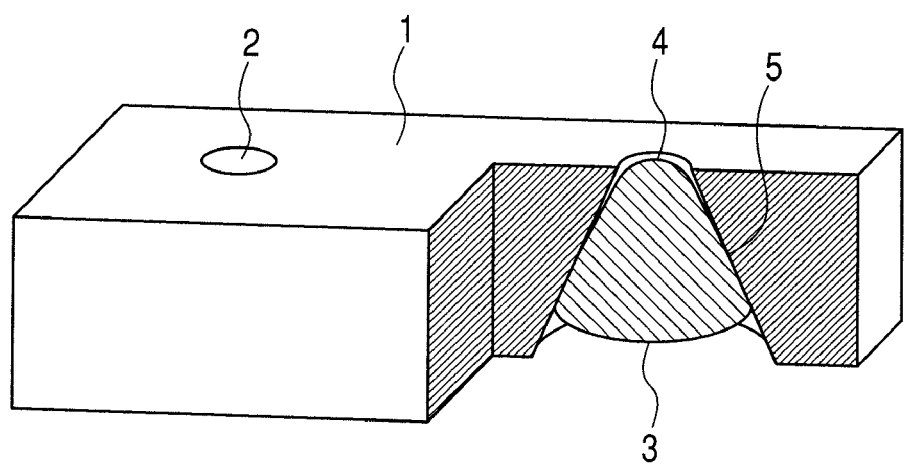
FIG. 5 is a view illustrating a substrate example with immobilized cells.

First, description is made, with reference to FIG. 5, on the cells immobilized in the through-holes in the substrate according to the present embodiment. The substrate 1 for immobilizing the cells is beforehand prepared, and the size of the opening 2 of the through-hole bored in the substrate is smaller than the diameter of the cell.

In the present invention, the phrase "immobilize in the through-hole" means to immobilize the cell in the substrate in a state that at least a portion of the cell is present in the through-hole. The whole of the cell may be present in the through-hole or the cell may hang out of the through-hole.

In the present embodiment, the cell 3 is bonded to the substrate 1 so as to block up the opening 2 of the through-hole, a portion 4 (hereinafter, refereed to as the "exposed portion," as the case may be) of the cell is exposed in the opening 2. The region (in FIG. 5, the region above the cell) in contact with the exposed portion 4 of the cell can be made to be a gas phase, and hence a beforehand-prepared microdroplet can be brought into direct contact with the exposed portion 4 of the cell by using an inkjet printer or the like. In this case, the portion in contact with the microdroplet is limited to the exposed portion 4 that is a portion of the cell. Additionally, as long as a microdroplet can be directly administered to the cell 4 as described above, the apparatus for administration is not limited to an inkjet printer, but for example, the electrospray method can also be used for administration.

On the other hand, the region on the opposite side (in FIG. 5, the lower side of the cell) to the exposed portion 4 of the cell 3 is the liquid phase region where the medium and the like are present. By making this region be a liquid phase, the drying of the cells can be prevented and the life of the cells can be maintained over a long period of time. This liquid phase may include, in addition to the medium, a buffer solution, an inorganic salt solution and the like.

The apparatus for introducing a substance of the present invention is assumed to mainly use animal cells, but can also use protoplastized plant cells. Additionally, in the present invention, both adherent cells and nonadherent cells can be used. Both cells isolated from living body and cultured cells can be used as long as such cells can maintain life during the period of observation. From the viewpoint of the easiness in blocking up the through-holes, the present apparatus preferably immobilizes only one cell in one through-hole in the substrate. From such a viewpoint, the cells distributed so as to be isolated from each other are preferably used. However, as long as clumps of cells (for example, tissue fragments and spheroids) can be immobilized so as to block up the through-holes, such clumps of cells can also be used. Various methods have hitherto been reported for the method for immobilizing cells, and hence any of these methods may be selected according to need; in this connection, the following methods are more preferable bonding modes. However, the method for immobilizing cells is not limited to the following methods if any other methods having the similar effects are found.

Cell-Immobilization Method Example 1

Figure 6:
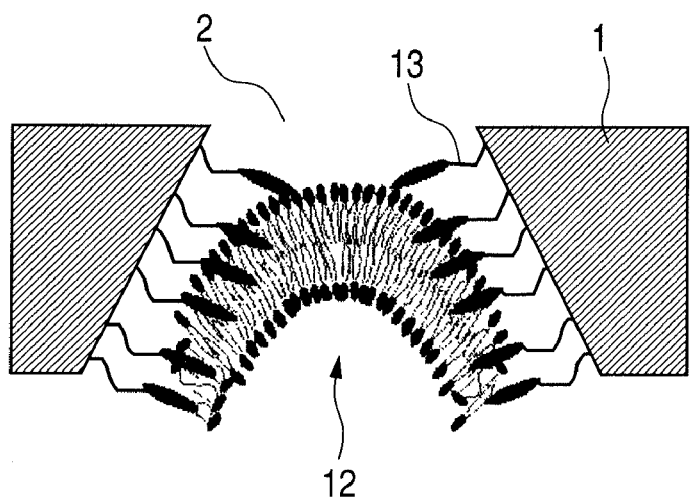
FIG. 6 is a view illustrating a cell-immobilization method example 1.

Hereinafter, description is made with reference to FIG. 6. In the present example, first, the substrate 1 is coated with bovine serum albumin and the substrate surface is modified with amino groups. Next, through the intermediary of the amino groups, the whole surface of the substrate 1 or the inner wall surface of the through-holes is modified with SUNBRIGHT OE-02CS (trade name, manufactured by NOF Corp., chemical name: α-succinimidyloxysuccinyl ω-oleyloxy polyoxyethylene) 13. Next, the surface opposite to the surface having the through-hole openings 2 of the SUNBRIGHT OE-020CS modified substrate 1 is brought into contact with a suspension of the cell 12 so as to be added with the suspension, and then by suction from the side having the through-hole openings 2 of the substrate 1, the cell 12 is drawn to stick to the through-hole of the substrate. The cell 12 drawn to stick is immobilized with SUNBRIGHT OE-020CS 13 so as to block up the through-hole of the substrate (FIG. 6).

Cell-Immobilization Method Example 2

Figure 7:
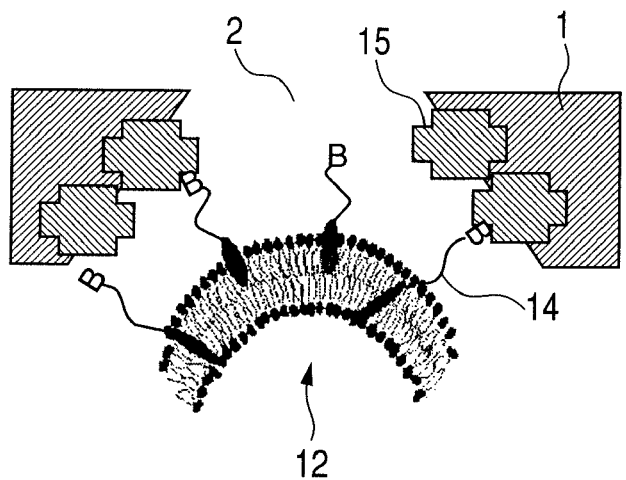
FIG. 7 is a view illustrating a cell-immobilization method example 2.

Hereinafter, description is made with reference to FIG. 7. First, SUNBRIGHT OE-020CS (trade name, manufactured by NOF Corp., chemical name: α-succinimidyloxysuccinyl w-oleyloxy polyoxyethylene) is bonded with a biotin derivative having an amino group to form a combination. Next, the combination 14 is added to a cell suspension. Herewith, the combination 14 is bonded to the cell surface and the cell surface is modified with biotin. Next, a substrate 1 having through-holes is coated with avidin 15. Successively, the suspension of the biotin-modified cell 12 is brought into contact with the surface opposite to the surface having the through-hole openings 2 of the avidin-coated substrate 1, and then by suction from the side having the through-hole openings 2 of the substrate 1, the cell is drawn to stick to the through-hole of the substrate. The biotin-modified cell drawn to stick is bonded to the avidin on the substrate surface to be immobilized so as to block up the through-hole.

Cell-Immobilization Method Example 3

Figure 8:
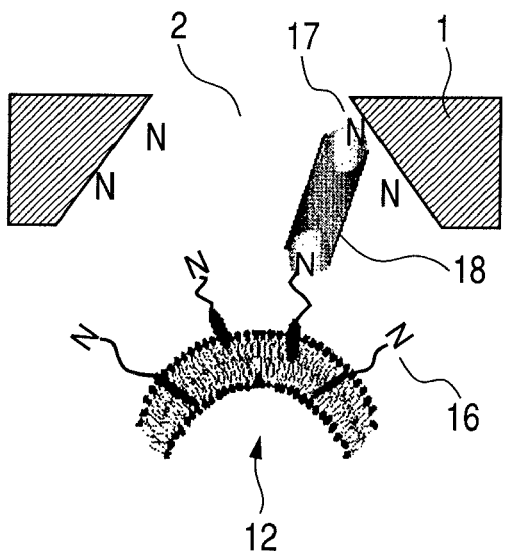
FIG. 8 is a view illustrating a cell-immobilization method example 3.

Hereinafter, description is made with reference to FIG. 8. First, the substrate 1 having through-holes is coated with bovine serum albumin and the substrate surface is modified with amino groups 17. By cross-linking the amino groups 17 on the substrate surface with the amino groups present on the cell membrane surface by using an amino group-reactive divalent cross-linking agent 18, the cell 12 is immobilized so as to block up the through-hole. Here, the cell surface is modified with amino groups by adding SUNBRIGHT DSPE-020PA (trade name, manufactured by NOF Corp., chemical name: N-aminopropyl polyethylene glycol carbamil distearoylphosphatidylethanolamine) 16 to a cell suspension, and the amino groups are utilized as the amino groups belonging to the cell. Alternatively, the amino groups originated from the cell membrane protein may also be utilized. Next, a suspension of the cell 12 is brought into contact with the surface opposite to the surface having the through-hole openings 2 of the substrate 1, and then by suction from the side having the through-hole openings 2 of the substrate 1, the cell is drawn to stick to the through-hole of the substrate. The amino groups of the amino group-modified cell drawn to stick are bonded with the amino groups 17 on the substrate surface by using the cross-linking agent 18, and thus the cell is immobilized so as to block up the through-hole.

Cell-Immobilization Method Example 4

Figure 9:
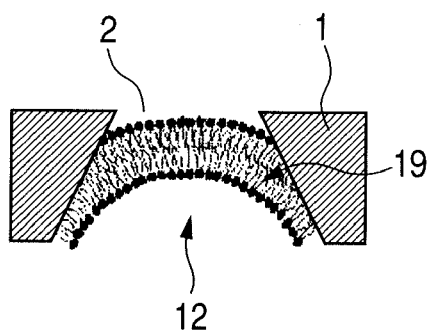
FIG. 9 is a view illustrating a cell-immobilization method example 4.

Hereinafter, description is made with reference to FIG. 9. A suspension of the cell 12 is brought into contact with the surface opposite to the surface having the openings 2 of the substrate 1 having the through-holes and being hydrophobic on the surface thereof, and then by suction from the side having the through-hole openings 2 of the substrate, the cell is drawn to stick to the through-hole of the substrate. The cell membrane 19 of the cell drawn to stick and the hydrophobic surface of the substrate 1 interact to be bonded to each other, and consequently, the cell 12 is immobilized so as to block up the through-hole of the substrate.

Cell-Immobilization Method Example 5

Figure 10:
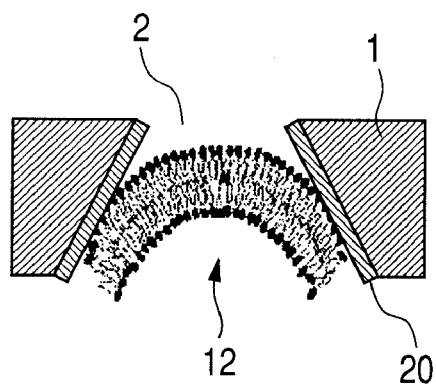
FIG. 10 is a view illustrating a cell-immobilization method example 5.

Hereinafter, description is made with reference to FIG. 10. Here, an adherent cell is used as the cell. A substrate having through-holes is coated with an extracellular matrix protein (EMC) 20 such as collagen, fibronectin or vitronectin, or a modified ECM. A suspension of the cell 12 is brought into contact with the surface opposite to the surface having the openings 2 of the substrate 1, and then by suction from the side having the openings of the substrate, the cell 12 is drawn to stick to the through-hole so as to block up the through-hole. Thereafter, the thus processed substrate is allowed to stand still for approximately 30 minutes to 2 hours to make the cell adhere to the through-hole.

Embodiment 3

Figure 1:
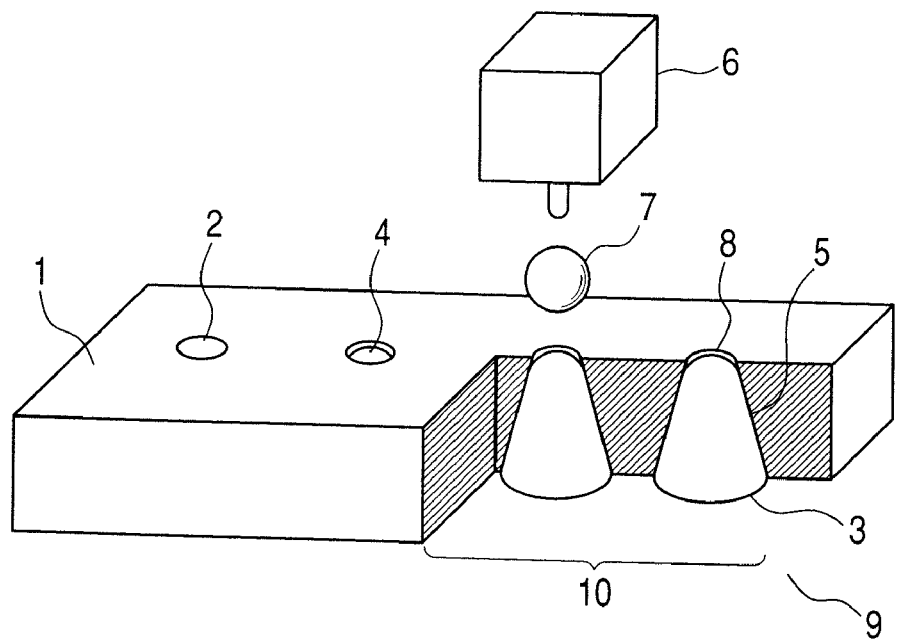
FIG. 1 is a schematic view of an immobilized cell chip for use in administering a microdroplet discharged from an inkjet printer to a portion of a cell.

Method for Administering a Microdroplet to a Portion of the Cell Immobilized in the Substrate As shown in FIG. 1, by using a microdroplet discharging apparatus typified by an inkjet printer, a microdroplet of a solution of a substance intended to be tested is added to a portion of the through-hole opening 2 of the substrate 1. The size of the microdroplet preferably falls in a range from 200 fL to 1 pL, and a volume of approximately 1 pL is practical from the viewpoint of being capable of using a commercially available inkjet printer.

In the periphery of the opening 2, a portion 4 of the immobilized cell 3 is exposed, and the solution given as a microdroplet 7 is administered to the portion 4 of the cell. Additionally, by adding a cell membrane substance-permeation accelerator to the solution forming the microdroplet 7, a hole of approximately 30 nm can be bored in the cell membrane portion of the portion 4, and thus a desired substance can be introduced into the cell through this hole. In other words, by using a cell membrane substance-permeation accelerator, a microhole can be bored in a limited portion of the immobilized cell. In this way, the damage to the cell caused by introducing a substance into the cell can be reduced. Examples of possible cell membrane substance-permeation accelerator include streptolysin-O (SLO) and surfactants. For the utilization conditions of SLO, above-described Japanese Patent Application Laid-Open No. 2006-129798 and the following paper can be referred to: Iwan Walev et al., Delivery of proteins into living cells by reversible membrane permeabilization with streptolysin-O, Proceedings of the National Academy of Sciences of the United States of America, Vol. 98, No. 6, pp. 3185 to 3190.

It is to be noted that illustrated in FIG. 1 are a bonding portion 5 between the cell and the substrate, a head 6 of an inkjet printer, a microdroplet 8 made to land on a portion of a cell, medium 9, and a three-dimensional section-representing portion 10 of a substrate portion around a through-hole.

Example

Figure 11:
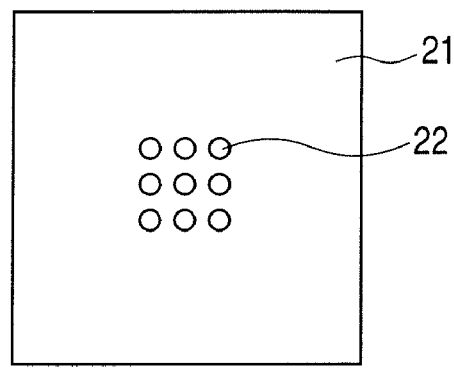
FIG. 11 is a view illustrating a substrate with through-holes bored therein.
Figure 12:
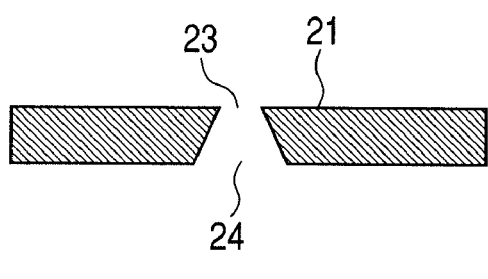
FIG. 12 is a view illustrating a section of the substrate with the though-holes bored therein.
Figure 13:
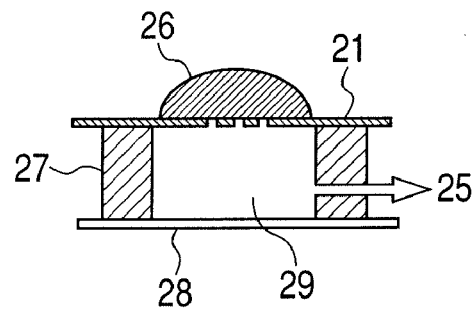
FIG. 13 is a view illustrating a cell-suction apparatus.
Figure 14:
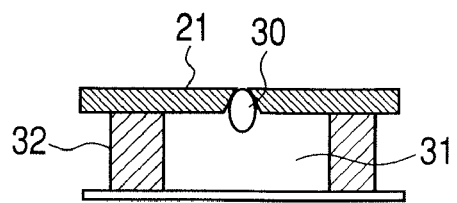
FIG. 14 is a view illustrating a setting of a cell-immobilizing support at the time of administering microdroplets.

As shown in FIG. 11, in the center of a 25-μm thick 3-cm square polyimide film 21 (KAPTON®, manufactured by Toray-DuPont Co., Ltd.) by using a heretofore well known method using a femtosecond pulse laser machining apparatus, nine (3×3, the intercenter distance between the through-holes is 0.5 mm) truncated circular cone-shaped through-holes 22 each having a front side opening (23 in FIG. 12) of approximately 5 μm in diameter and a back side opening (24 in FIG. 12) of approximately 15 μm in diameter are bored. The film is subjected to an oxygen plasma processing, and then soaked in a 1% bovine serum albumin solution at room temperature for 16 hours. The film is washed with water and dried, and then soaked in a 0.1 mM solution of SUNBRIGHT OE-020CS (chemical name: α-succinimidyloxysuccinyl w-oleyloxy polyoxyethylene, manufactured by NOF Corp.) at room temperature for 2 hours. After soaking, the film is washed with water. Human leukemia cell, THP-1 cell (obtained from Dainippon Sumitomo Pharma Co., Ltd.), is washed with a phosphate buffer physiological salt solution (PBS) 29, and thereafter suspended in the same solution to prepare a suspension adjusted to a cell concentration of $1 \times 10^6$ cells/ml. Next, as shown in FIG. 13, a silicon chamber 27 and a slide glass 28 are disposed on a not-shown microscope stage, and the film 21 is disposed on this chamber 27 so as for the back side of the film 21 to face upward. Thereafter, the suspension 26 is placed as an appropriate volume of microdroplet on the film 21, and immediately thereafter the interior of the chamber is sucked with a suction pump 25. And, with a microscopic observation, the cell is observed to be immobilized in the through-hole. The cell-immobilized film is soaked in PBS to be washed. Successively, as shown in FIG. 14, the cell 30-immobilized film 21 is disposed, with its back side facing downward, on the silicon chamber 32 with serum-free RPMI 1640 medium 31 placed therein in such a way that no air is incorporated. An inkjet printer (manufactured by Canon Inc.) is filled with the following solution, and microdroplets are added dropwise toward the through-hole openings of the cell-immobilized support under high humidity. The support is allowed to stand still under high humidity at 37° C. for 15 minutes, and thereafter the introduction of the substance into the cells is observed by observing the cells with the aid of a fluorescence microscopic observation.

(Filling Solution to Inkjet Printer)

In a calcium ion-free Hanks equilibrium salt buffer solution (pH 7.2) added with a 30-mM Hepes buffer solution, SLO (final concentration: 20 to 80 ng/ml) and an FITC-labeled antibody fragment (F(ab')$_2$) (final concentration: 1 μM) are added.

According to the above-described preferred embodiments of the present invention, by imparting a microdroplet only to a portion of a cell by using an inkjet printer or the like, even when a substance is administered simultaneously with the processing to enhance the efficiency of the introduction of a substance into cells, the damage given to the cells can be limited to the smallest limit, and the precision of the substance evaluation can be enhanced. Further, inexpensive and fast droplet imparting apparatus such as an inkjet printer can be applied, and hence the present invention is appropriate for multiple-specimen processing. In other words, there can be provided the above-described immobilized cell array apparatus, having a high throughput and a quality ensuring a high evaluation precision, for use in evaluation of the function of the candidate substance to the cells, and a method for producing the array apparatus.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2006-016414 filed on Jan. 26, 2007, which is hereby incorporated by reference herein.

The invention claimed is:

1. An apparatus for introducing a substance into a cell comprising:
a cell-immobilizing support comprising a substrate having at least one through-hole penetrating the substrate from a first side to a second side and comprising a cell immobilized in the through-hole so as to block up the through-hole;
a liquid phase region present in contact with the first side of the support and comprising a medium of the cell;
a gas phase region present in contact with the second side of the support; and
a mechanism present so as to face the second side of the support and is configured to impart a microdroplet to a portion of the cell, wherein the cell is exposed to the gas phase in an opening on the second side.

2. The apparatus for introducing a substance into a cell according to claim 1, wherein only one cell is immobilized in each said through-hole.

3. The apparatus for introducing a substance into a cell according to claim 1, wherein the microdroplet comprises a cell membrane substance-permeation accelerator.

4. The apparatus for introducing a substance into a cell according to claim 1, wherein the cell is immobilized using a cell-anchoring material.

* * * * *